United States Patent [19]

Peer

[11] 4,349,569
[45] Sep. 14, 1982

[54] METHOD OF CULTURING *LACTOBACILLUS ACIDOPHILUS*

[75] Inventor: Herbert R. Peer, Storm Lake, Iowa

[73] Assignee: TransAgra Corporation, Memphis, Tenn.

[21] Appl. No.: 873,156

[22] Filed: Jan. 27, 1978

Related U.S. Application Data

[63] Continuation-in-part of Ser. No. 711,454, Aug. 4, 1976, abandoned.

[51] Int. Cl.³ ............... A23C 9/123; C12N 15/00; C12N 1/36; C12N 1/20
[52] U.S. Cl. .................... 426/43; 435/172; 435/245; 435/253
[58] Field of Search ............ 435/245, 854, 253, 172; 426/34, 41, 43, 42

[56] References Cited

U.S. PATENT DOCUMENTS 3,343,962  9/1967  Peer ........................... 426/253 X
3,497,359  2/1970  Peer ........................... 426/41 X

OTHER PUBLICATIONS

Webb et al., By Products From Milk, 2nd Ed., The Avi Publishing Co., Inc., Westport, Conn. 1970, (pp. 24-29, 32 & 33).
Manual For Dairy Manufacturing Short Courses, Kurtz Bros., Clearfield, Pa. 1956 (pp. 56-57).

*Primary Examiner*—David M. Naff
*Attorney, Agent, or Firm*—Laurence R. Brown

[57] ABSTRACT

*Lactobacillus acidophilus* is cultured by special process steps to derive a strain of organisms having a length of over ten microns and a tough stable outer hide, and which produce high acidity above 1.5%, exhibit a characteristic odor, and are tolerant to metallic salts such as cobalt carbonate. They are cultured in a transfer process from starter organisms of different characteristics to develop the improved strain which retains its characteristics in the presence of metallic salts added to the nutrient before incubation and are free of a tendency to clump.

2 Claims, 6 Drawing Figures

METHOD OF CULTURING *LACTOBACILLUS ACIDOPHILUS*

This application is a continuation-in-part of U.S. Ser. No. 711,454 filed Aug. 4, 1976, now abandoned.

This invention relates to the culture of *Lactobacillus acidophilus* and more particularly it relates to such culture in the presence of metallic salts such as cobalt carbonate.

BACKGROUND OF THE INVENTION

In the production of cultured whey products such as described in my U.S. Pat. Nos. 3,343,962, Sept. 26, 1967 and 3,497,359, Feb. 24, 1970 a mother culture is produced by culturing *Lactobacillus acidophilus* in a milk nutrient base in the presence of cobalt carbonate. This conditions the organisms to become tolerant to a higher acidity condition than usually expected from *Lactobacillus acidophilus*, a desirable characteristic.

It has now been found however that at least some *Lactobacillus acidophilus* strains are sensitive to addition of metallic ions such as obtained in the presence of cobalt carbonate, a phenomenon that may be termed metal poisoning. This is evidenced by lower acidity, dwarfing and clumping of the organisms.

Usual strains of *Lactobacillus acidophilus* can be expected to have a percent of acidity, expressed as Lactic acid, below 1.5. The desired strains are characterized by acidity rise to the order of 2% or greater.

The organism physical characteristics of a typical laboratory strain of *Lactobacillus acidophilus* show a size of three to five microns with thin rod-like structure, some bent and L-shaped and with a more or less loosely held, almost transparent outer sheath that tends to collapse and wrinkle.

OBJECTS OF THE INVENTION

It is therefore a general object of this invention to develop strains of *Lactobacillus acidophilus* that are resistant to the presence of metallic ions.

A more specific object of the invention is to produce *Lactobacillus acidophilus* strains more resistant to Lactic acid.

Another object of the invention is to produce *Lactobacillus acidophilus* strains with improved physical characteristics exhibited in the form of large organisms of the order of 10 microns or larger having thick rod-like shape and a firm skin structure.

A still further object of the invention is to produce *Lactobacillus acidophilus* strains treated with metallic ions that are identified by the characteristic that they do not cluster.

BRIEF DESCRIPTION OF THE INVENTION

Therefore, in accordance with this invention a *Lactobacillus acidophilus* commercial or laboratory strain of small, fragile, acid and metal ion sensitive organisms is cultured and transmuted into a strain of enlarged, toughened organisms tolerant to higher acidity and the presence of metal ions, which are free from a clustering characteristic in the presence of metal ions or after being previously treated with metal ions. These organisms permanently retain their characteristics after the transmutations.

The culture process comprises a sequence of several successive culture transfer procedure (herein called serial transfers) where the organisms are cultured in milk in the presence of a low density metallic carbonate and an ammonium compound. This transfer transmutes the organisms into a strain that withstands higher metallic ion concentrations, that exhibits better physical stamina, and that is identified by different characteristics of size, shape and skin texture and a characteristic odor.

THE DRAWING

FIG. 1 of the drawings shows comparative microphotographs of a typical laboratory strain of *Lactobacillus acidophilus* organisms at 10,000 times magnification;

FIG. 2 of the drawings shows similar comparative microphotographs of a partially developed strain of *Lactobacillus acidophilus* organisms having an outer shell structure that tends to collapse and wrinkle;

FIG. 3 of the drawings shows similar comparative microphotographs of a strain of *Lactobacillus acidophilus* organisms produced by the teachings of this invention that has a large size, tough outer shell, high acidity characteristic and characteristic odor; and FIGS. 4, 5 and 6 show comparative microphotographs at 500 times magnification with the presence, partial presence, and absence of the clumping characteristic of such organisms.

DETAILED DESCRIPTION OF THE INVENTION

The general process deriving starter mixtures through developing initial cultures from a transfer in accordance with the conventional procedure for carrying culture stocks, herein called serial transfer of an initial mother culture stock treated with a metallic carbonate from a laboratory *Lactobacillus acidophilus* strain is set forth in the before mentioned U.S. Patents. A starting commercial source of Lactobacillus acidophilus can be obtained from Chr. Hansen's Lab. Inc., Milwaukee, Wisc., in freeze dried powder form. Other strains such as ATCC strain 4356-1 or 4357 do not seem to exhibit the same characteristics and there is no evidence that the transmutation by this invention occurs. The currently available strain is described in the "American Cultured Dairy Products Journal", Vol. 10, No. 1, Feb. 1975 in a study by E. M. Mikolojcik and I. Y. Hamdon. Also it is known that such mother cultures are preserved by storage at 20° to 50° F. and used for producing stock cultures, pre-starter cultures, and whole milk starter cultures. This develops a typical starting strain of *Lactobacillus acidophilus* which is transmuted into a superior strain by this invention.

A control culture of the starting strain of *Lactobacillus acidophilus* can be prepared from this aforementioned commercial strain by autoclaving 150 ml of commercial skim milk at 5 psi (0.775 p/cm$^2$) for 20 minutes, cooling to 37° C. and inoculating with 0.5 gram of the commercial powder stock and incubating at 37 to 39° C. for 24 hours.

Observation under a microscope will show the organisms are clumped together when viewed in a distilled water suspension dilution of 50 to one. To observe densities, samples may be brought to 0.1% acidity with addition of NaOH solution which releases the clumping. The tendency of the organisms is to clump at higher acidity. The organisms are small in the order of three to five microns in length with many curved and L-shaped forms as typified by FIGS. 1 and 2. The percentage of acidity is low of the order of 1.2%.

By serial transfer through a number of culture cycles in the presence of cobalt carbonate, in accordance with this invention, the cell size increases to the order of 10 microns, the acidity rises to about 1.8% and the clumping condition disappears. These features are retained permanently through further serial transfers, the outer shell characteristics change by the strain as evidence of transmutation.

When the samples are cultured in the presence of 100 to 500 ppm of cobalt carbonate added to the milk before autoclaving, the acidity does not rise, the organisms are retarded in growth and the clumping condition persists through many transfers. Also the condition persists even when the cobalt carbonate is withdrawn through a further series of transfers. It is thus evident that the strains developed in the presence of cobalt carbonate have characteristics of small size, low acid transfer of organisms and wrinkled outer shell which becomes fixed and permanent by some unknown conditioning mechanism.

In order to provide a stronger organism for use in the presence of cobalt carbonate or like metal salts it has been found in accordance with this invention that the initial treatment of the organisms can produce a strain of organisms with improved properties that will not deteriorate in the presence of metal ions such as produced from cobalt carbonate processed with milk nutrient or the like.

MOTHER CULTURES

Two mother cultures were established, the first mother culture (M1) as follows
  (a) autoclave 150 ml of commercial skim milk at 5 psi for 20 minutes,
  (b) cool to 37° C. and inoculate with 0.5 gram of the Hansen's strain of commercial freeze-dried *Lactobacillus acidophilus* powder,
  (c) incubate at 37°-39° C. for 24 hours.

The second mother culture (M2) had step (a) modified as follows:
  (a') autoclaved as (a) carrying a concentration of 300 ppm cobalt carbonate.

Both mother cultures have about 1.3% acidity expressed as Lactic acid PH-3.9 and 1.75 billion/ml cell density and are completely clumped together as in FIG. 4 when viewed under the microscope in a distilled water suspension at a dilution of 50 to 1 and brought to 0.1% acidity with 0.1 N NAOH.

The organisms are small on the order of 3 to 5 microns in length and generally interspersed with curved and L-shaped forms.

INTERMEDIATE CULTURES

Further cultures were made by serial transfers from the mother cultures in the following manner:

In one set of cultures (I1) 150 ml samples of skim milk were autoclaved at 5 psi for 20 minutes and cooled to 37° C. before inoculation with 10 ml of mother culture M1 and incubation at 37° to 39° C. for 24 hours.

A second set of cultures (I2) were similarly formed but each sample carried 300 ppm cobalt carbonate when autoclaved, and mother culture M2 was used.

SERIALLY DEVELOPED CULTURE

Each intermediate culture was serially transferred daily over a five day period in the same fashion with transfers made directly without storage in refrigeration, and the first series (SD1) without cobalt carbonate, the second series (SD2) with.

The resulting first culture series SD1 showed the following characteristics:

| % Acidity | 1.2 | 1.5 | 1.8 | 2.1 | 2.1 |
|---|---|---|---|---|---|
| PH | 3.85 | 3.65 | 3.5 | 3.4 | 3.4 |
| Density/ml | $1.2 \times 10^9$ | $.5 \times 10^9$ | $.5 \times 10^9$ | $.7 \times 10^9$ | $.3 \times 10^9$ |

The second culture series SD2 (with cobalt carbonate) showed:

| % Acidity | 1.4 | 1.3 | 1.2 | 1.2 | 1.2 |
|---|---|---|---|---|---|
| PH | 3.8 | 3.7 | 3.8 | 3.8 | 3.8 |
| Density/ml | $1.4 \times 10^9$ | $1 \times 10^9$ | $.8 \times 10^9$ | $1 \times 10^9$ | $.9 \times 10^9$ |

Clumping was observed in both series through serial culture step 2. However, in the third transfer of the first culture series SD1, the clumping disappeared as the acidity rose to 1.8. The cells also increased in size to 10 to 15 microns, were straight and symmetrical with squared off ends and the cell surfaces appeared to have a thicker darker area. This persisted through the fifth transfer. The second culture series SD2 did not develop in this manner, nor did the acidity increase.

Clearly the evidence shows inhibition of normal growth in the presence of a metallic ion such as cobalt carbonate.

EXAMPLE 1-TRANSMUTED ORGANISMS

A further series of six serial transfers of the SD1 culture in the presence of cobalt carbonate showed that the characteristics continued without the clumping while producing high acidity, whereas the SD2 culture continues its characteristics. Thus, it is evident that a transmuted strain characteristic has been developed which reacts differently in the presence of metallic ions by the characteristics of increased acidity, freedom from clumping, predomination of organisms having different physical shape appearing larger and more vigorous and having higher resistance to the metal poisoning effect in the presence of the metallic ions.

Also the second culture series SD2 cultured with cobalt carbonate was serially transferred through eleven steps in the absence of cobalt carbonate without changing its basic characteristics showing that indeed the two serially developed cultures are different in permanently exhibiting their developed characteristics. The strain developed without addition of cobalt carbonate appears to be a superior strain which can be cultured in a higher acidic environment and thereafter is not subjected to the metal poisoning effect.

EXAMPLE II-TRANSMUTED ORGANISMS 150 ml skim milk was treated with 100 ppm cobalt carbonate and 1 gram ammonium chloride and autoclaved, brought to room temperature and inoculated with the SD2 serially transferred culture strain (with cobalt carbonate) after eleven serial transfers which exhibited the clumping characteristic.

The first transfer was free of the clumped condition and the large physical characteristics were exhibited.

Thus, the evidence shows the ammonium ion when added after the clumping strain is developed in the presence of the metallic ion transmutes the strain characteristics into those developed in the absence of the metallic ion.

To avoid coagulation of the milk the ammonium chloride was reduced to 0.5 gram, where partial clumping was observed.

The permanent characteristics were not retained since upon further series transfers the clumping returned and the organisms reverted to their small cell characteristics.

EXAMPLE III–CLUMPING FREE ORGANISMS

In this example the milk was treated with 100 ppm cobalt carbonate and a base comprising 1.5 grams ammonium lactate (to eliminate the chloride ion) before autoclaving, and inoculated with the clumping strain of *Lactobacillus acidophilus* cultured in the presence of cobalt carbonate as before described.

The ammonium lactate may be prepared by treating 100 ml tech lactic acid (88%) with 26° BE' ammonium hydroxide until the mixture is slightly basic and driving off excess ammonia by gentle heat reducing the volume of the reaction by evaporation to 100 ml. The chemical process is expressed as

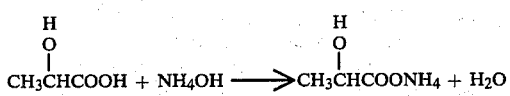

The first transfer of this example shows a positive shift to the larger forms of the improved strain free of clumping. However, this strain exhibits acidity of a lower range less than 1.5%.

EXAMPLE IV–TRANSMUTED ORGANISMS

Here the 150 ml skim milk was treated with 25 ppm cobalt carbonate and 2 grams ammonium lactate before autoclaving at 5 psi for 20 minutes. The cooled milk at 37° to 38° C. was inoculated with 0.5 gram of the dried commercial Hansen's *Lactobacillus acidophilus* strain and incubated at that temperature for 24 hours.

This mother culture without further transfer is unique in exhibiting large organisms (30% at 15 microns) and is only partially clumped with an organism density of 700 million/ml., a PH of 4.0 and acidity of 1.0% developing under further similar serial transfers a density of 450 million/ml., a PH of 3.7 and acidity of 1.6%.

With high concentrations of cobalt carbonate above 100 ppm there is a tendency to intimidate transmutation in the absence of an ammonium compound. It is noted the total organism protoplasm is increased with larger organisms and therefore the density count may decrease.

On the second serial transfer under the same conditions the culture is free of clumping and acidity rises sharply to the order of 2.5% and very large cells are observed (20 to 25 microns) with good body encapsulation (to be discussed hereinafter).

In the third transfer even with addition of more cobalt carbonate (100 ppm) and 1.5 grams ammonium lactate the number of organisms and acidity improves (1.7 billion and 2.7%). Thus, an improved strain of organisms is developed by initial treatment in the presence of an ammonium source, which strain is not intimidated or retarded in the presence of cobalt carbonate.

In this example it is observable that the presence of a base substance such as ammonium free of the chloride ion is a factor in both avoidance of clumping and in the development of an improved organism strain.

This series maintains the organism properties over the serial transfer process in the presence of 100 ppm of cobalt carbonate and 1 gram of ammonium lactate for 150 ml milk.

A characteristic odor is developed by this transmuted strain similar to that for the cultures defined in the above mentioned patents. This fragrance of *Lactobacillus acidophilus* strains is a physical property identifying an organism exhibiting certain favorable properties in the growth of animals and plants. Other *Lactobacillus acidophilus* strains than that herein and in said patents have a mildly unpleasant and cheese-like fragrance. The desired strains develop a pleasant fruity sweet acid fragrance.

EXAMPLE V 150 ml skim milk treated with 50 ppm cobaltous ammonium phosphate and two grams ammonium lactate exhibited substantially the same properties as the strain developed in Example IV above.

EXAMPLE VI

In a preferred method, 0.016 grams cobalt carbonate is dissolved in 4 ml ammonium lactate solution (0.5 grams ammonium lactate per ml.).

150 ml skim milk treated with 4 ml of this cobaltous ammonium lactate solution, in serial transfer, will maintain cobalt carbonate equivalent levels in excess of 100 ppm, with substantially the same properties as Example V.

Discussion

When ammonium lactate is introduced to the system of serial transfers involving cobalt carbonate there are substantial changes in the organism properties.

Improved strains of organisms can be transmuted to provide a characteristic odor, higher acidity, larger size and absence of clumping.

It is thought that the initial presence of free cobalt ion (100 ppm or above) during early development of acidity, in some way inhibits the respiratory function.

That is, as the acidity values increase from 0 to 1.2% (in the presence of cobalt ion), the clumping phenomenon progressively increases until it becomes total, and further acid production is thus diminished.

The introduction of ammonium ion (ammonium lactate) in some way masks the cobalt ion so that clumping is avoided, presumably thru the formation of some coordination complex such as $CO(NH_3)_6^{++}$ or $CO(NH_3)_6^{+3}$ [Hexammonium II or III].

It is deduced that the initial laboratory strain is an organism specially adapted for use in milk products, and that it provides new strains having distinctive properties retained after development by transmutation in a serial transfer process.

The physical properties of a transmuted strain may be developed to increase the size and sturdiness of the organism.

Treatment by a metal salt tends to permanently change organism structure which otherwise reverts in the serial transfer process.

DESCRIPTION OF THE DRAWING

With reference to the drawing, the photographs show the characteristics of *Lactobacillus acidophilus*.

FIG. 5 shows an intermediate phase and FIG. 4 shows the clumping phenomena.

Figure 1:
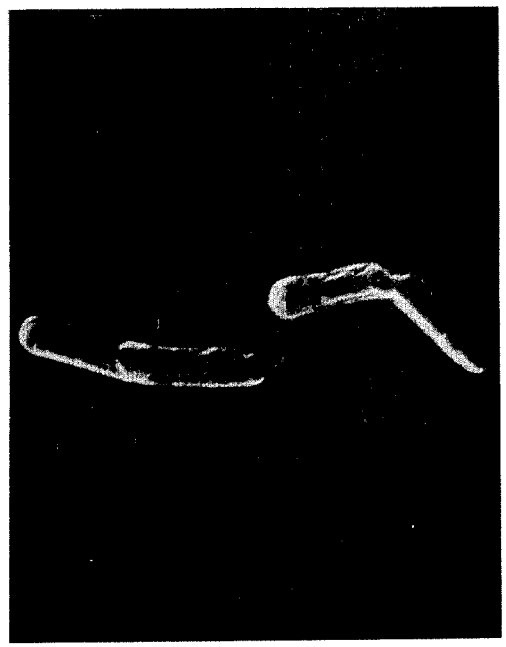
FIG. 1 shows the starter culture organisms which are three to five microns in length and many are curved or bent. The wall structure tends to collapse or wrinkle.
Figure 2:
FIG. 2 shows the early stages of cobalt ammonium lactate system treatment, where the organism has developed a greater length in the order of ten microns or greater.
Figure 3:
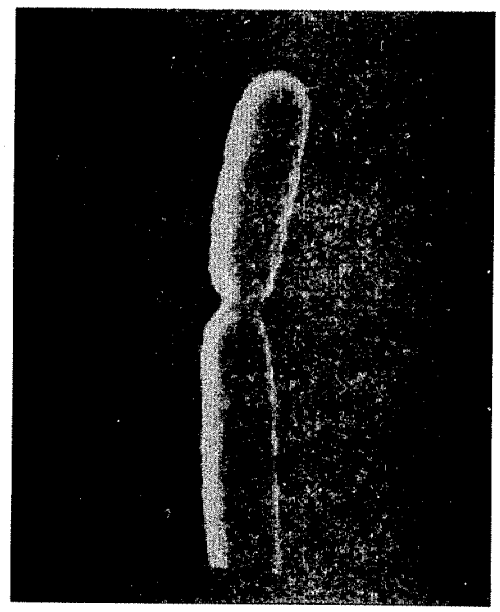
FIG. 3 shows the organisms as developed by this invention having lengths greater than ten microns and a firm outer shell, and generally straight.
Figure 4:
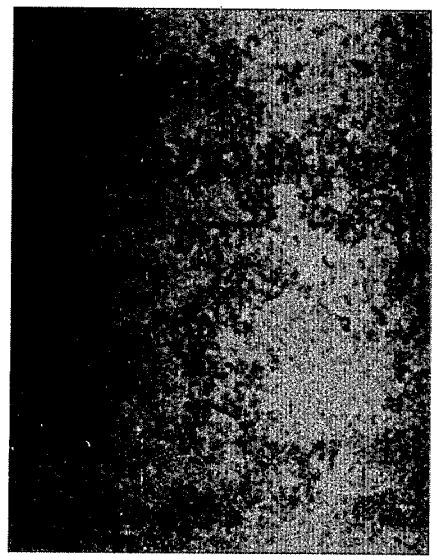
FIGS. 4, 5 and 6 are comparative photographs exhibiting the freedom from clumping characteristics achieved by the invention in FIG. 6.
Figure 5:
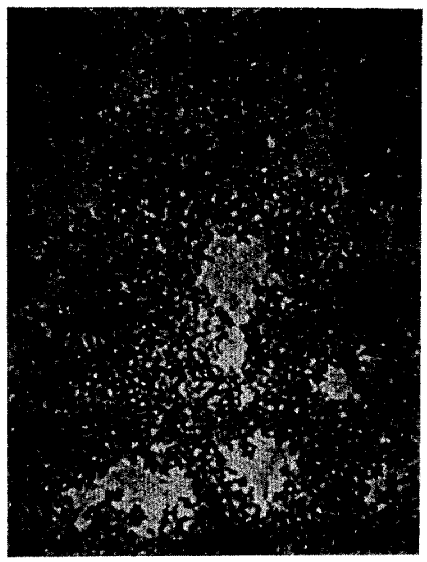
Figure 6:
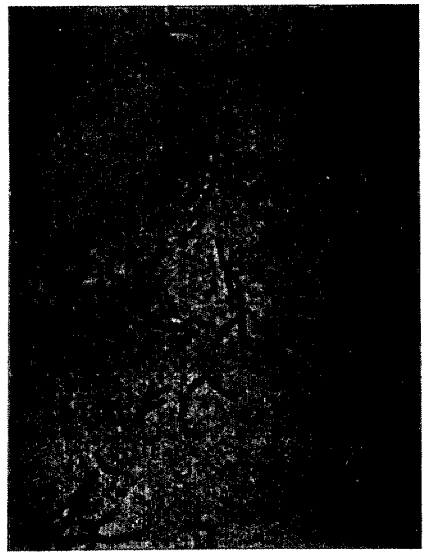

Transmutation to the desired characteristic permanently retained occurs when a sharp transition to high acidity takes place. These characteristics with identifying odor are physically seen by larger cell size with better defined outer shells and straight with squared off ends, which are free from clumping, and most important which are not sensitive to the presence of metallic ions such as presented by cobalt carbonate.

Having therefore described the preferred embodiments of the invention, those novel features believed descriptive of the spirit and scope of the invention are set forth with particularity in the appended claims.

What is claimed is:

1. A process of eliminating the metal poisoning effect evidenced by the tendency to clump exhibited by *Lactobacillus acidophilus* when cultured in the presence of cobalt carbonate comprising the steps of, (A) selecting a strain of *Lactobacillus acidophilus* of a size about three to five microns that clumps when exposed to the presence of cobalt carbonate in a milk nutrient base, (B) culturing said *Lactobacillus acidophilus* in a milk nutrient base in the presence of cobalt carbonate to produce an initial mother culture, (C) inoculating the mother culture in a nutrient culture medium consisting essentially of milk and cobalt carbonate with an added ammonium lactate, (D) culturing the inoculated mother culture of step (C) through a sequence of a plurality of culture cycles to obtain an improved mother culture by inoculating the nutrient medium with the culture obtained from the next preceding culture cycle to produce after a plurality of cycles *Lactobacillus acidophilus* organisms which have a size of about 10 to 15 microns and which do not clump when cultured in the presence of cobalt carbonate and which exhibits an acidity in excess of 1.75%, and (E) thereafter culturing the improved *Lactobacillus acidophilus* mother culture obtained from step (D) through a sequence of a plurality of culture cycles in the presence of cobalt carbonate wherein said 10 to 15 micron size and the freedom from clumping is maintained and the total organism protoplasm that may be produced in the culture process is increased.

2. The process of claim 1 wherein the ammonium lactate is present in an amount of about 1.5 grams per 150 ml of skim milk culture medium.

* * * * *